(12) United States Patent
Polli et al.

(10) Patent No.: US 8,719,043 B2
(45) Date of Patent: May 6, 2014

(54) DRUG AUTHENTICATION

(75) Inventors: James E. Polli, Ellicott City, MD (US);
Stephen W. Hoag, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 1288 days.

(21) Appl. No.: 10/572,912

(22) PCT Filed: Sep. 22, 2004

(86) PCT No.: PCT/US2004/030977
§ 371 (c)(1),
(2), (4) Date: Nov. 29, 2006

(87) PCT Pub. No.: WO2005/031302
PCT Pub. Date: Apr. 7, 2005

(65) Prior Publication Data
US 2007/0086625 A1 Apr. 19, 2007

Related U.S. Application Data

(60) Provisional application No. 60/504,774, filed on Sep. 22, 2003.

(51) Int. Cl.
*G06F 19/00* (2011.01)
(52) U.S. Cl.
USPC .............................................................. 705/2
(58) Field of Classification Search
USPC .............................................................. 705/2
See application file for complete search history.

(56) References Cited

U.S. PATENT DOCUMENTS

| | | | |
|---|---|---|---|
| 4,957,906 A | | 9/1990 | Yoshikumi et al. |
| 5,859,703 A | * | 1/1999 | Aldridge et al. ............... 356/319 |
| 6,458,595 B1 | | 10/2002 | Selinfreund |
| 6,765,212 B2 | * | 7/2004 | Goetz et al. ............... 250/339.11 |
| 6,771,369 B2 | * | 8/2004 | Rzasa et al. .................. 356/326 |
| 6,907,351 B2 | * | 6/2005 | Julia et al. ........................ 702/23 |
| 7,528,957 B2 | * | 5/2009 | Lewis et al. ................... 356/419 |
| 2002/0155541 A1 | | 10/2002 | Naughton et al. |
| 2003/0014647 A1 | * | 1/2003 | Bourrieres et al. ........... 713/185 |

(Continued)

FOREIGN PATENT DOCUMENTS

| | | |
|---|---|---|
| GB | 23 347 739 | 9/2000 |
| WO | WO 96/15428 | 5/1996 |

(Continued)

OTHER PUBLICATIONS

US Food and Drug Administration (FDA), Scale-up and Post-Approval Changes Guidance for Immediate Release Products, Nov. 30, 1995.*

(Continued)

*Primary Examiner* — Michael Fuelling
(74) *Attorney, Agent, or Firm* — Marianne Fuierer; Moore & Van Allen, PLLC

(57) ABSTRACT

A method is disclosed to verify and identify pharmaceutical products through their product signatures in order to combat counterfeiting and reduce dispensing errors, using methods such as near infrared spectroscopy. Furthermore, in order actively evade pharmaceutical product counterfeiting, a method is disclosed where an amount of one or more of the inactive ingredients is varied over time; the variation provides a different product signature, but falling within a level deemed permissible by a regulatory body.

14 Claims, 10 Drawing Sheets

Table 10. Schematic of use within the commercial pipeline

(56) References Cited

U.S. PATENT DOCUMENTS

| | | |
|---|---|---|
| 2003/0028328 A1 | 2/2003 | Julia et al. |
| 2003/0123050 A1 | 7/2003 | Selinfreund |
| 2004/0021861 A1* | 2/2004 | Lewis et al. ............... 356/326 |
| 2006/0015536 A1* | 1/2006 | Buchanan et al. ........... 707/200 |
| 2006/0062734 A1 | 3/2006 | Melker |
| 2006/0283931 A1* | 12/2006 | Polli et al. ................. 235/375 |
| 2012/0013734 A1* | 1/2012 | Ranieri et al. ............... 348/125 |

FOREIGN PATENT DOCUMENTS

| | | |
|---|---|---|
| WO | WO 01/03646 | 1/2001 |
| WO | WO 2005/028577 | 3/2005 |
| WO | WO 2005/031302 | 4/2005 |

OTHER PUBLICATIONS

Olsen et al., "Screening for Counterfeit Drugs Using Near-Infrared Spectroscopy," Pharmaceutical Technology North America, Jun. 2002, 26: 62-71.*

Anderson, M., et al., "Monitoring a film coating process for tablest using near infrared reflectance spectrometry", Journal of Pharmaceutical and Biomedical Analysis, vol. 20., No. 1-2, Jan. 6, 1999, pp. 27-37.

Scafi, S.H.F., et al., "Identification of counterfeit drugs using near-infrared spectroscopy", The Analyst, vol. 126, 2001, pp. 2218-2224.

Rodionova, et al., "NIR spectrometry for counterfeit drug dtection", Analytica Chimica Acta, Elsevier, Amsterdam, NL., vol. 549, No. 1-2, Sep. 6, 2005, pp. 151-158, XP005029826 ISSN: 003-2671. *p. 152*.

* cited by examiner

Table 1. Level 1 Component and Composition Changes for Immediate Release Oral Solid Dosage Forms

| Excipient | Percent Excipient (w/w) Out of Total Target Dosage Form Weight |
|---|---|
| Filler | +/- 5% |
| Disintegrant starch other | +/- 3% +/- 1% |
| Binder | +/- 0.5% |
| Lubricant calcium or magnesium stearate other | +/- 0.25% +/- 1% |
| Glidant talc other | +/- 1% +/- 0.1% |
| Film coat | +/- 1% |

Table 2. Level 2 Component and Composition Changes for Immediate Release Oral Solid Dosage Forms

| Excipient | Percent Excipient (w/w) Out of Total Target Dosage Form Weight |
|---|---|
| Filler | +/- 10% |
| Disintegrant starch other | +/- 6% +/- 2% |
| Binder | +/- 1% |
| Lubricant calcium or magnesium stearate other | +/- 0.5% +/- 2% |
| Glidant talc other | +/- 2% +/- 0.2% |
| Film coat | +/- 2% |

Figure 1

Table 3. Level 3 Component and Composition Changes for Immediate Release Oral Solid Dosage Forms

| Excipient | Percent Excipient (w/w) Out of Total Target Dosage Form Weight |
|---|---|
| Filler | Greater than +/- 10% |
| Disintegrant starch other | Greater than +/- 6% Greater than +/- 2% |
| Binder | Greater than +/- 1% |
| Lubricant calcium or magnesium stearate other | Greater than +/- 0.5% Greater than +/- 2% |
| Glidant talc other | Greater than +/- 2% Greater than +/- 0.2% |
| Film coat | Greater than +/- 2% |

Table 4. Level 1 Component and Composition Changes for Modified Release Oral Solid Dosage Forms (nonrelease controlling excipient)

| Excipient | Percent Excipient (w/w) Out of Total Target Dosage Form Weight |
|---|---|
| Filler | +/- 5% |
| Disintegrant starch other | +/- 3% +/- 1% |
| Binder | +/- 0.5% |
| Lubricant calcium or magnesium stearate other | +/- 0.25% +/- 1% |
| Glidant talc other | +/- 1% +/- 0.1% |
| Film coat | +/- 1% |

Figure 2

Table 5. Level 2 Component and Composition Changes for Modified Release Oral Solid Dosage Forms (nonrelease controlling excipient)

| Excipient | Percent Excipient (w/w) Out of Total Target Dosage Form Weight |
|---|---|
| Filler | +/- 10% |
| Disintegrant<br>starch<br>other | <br>+/- 6%<br>+/- 2% |
| Binder | +/- 1% |
| Lubricant<br>calcium or magnesium stearate<br>other | <br>+/- 0.5%<br>+/- 2% |
| Glidant<br>talc<br>other | <br>+/- 2%<br>+/- 0.2% |
| Film coat | +/- 2% |

Table 6. Level 3 Component and Composition Changes for Modified Release Oral Solid Dosage Forms (nonrelease controlling excipient)

| Excipient | Percent Excipient (w/w) Out of Total Target Dosage Form Weight |
|---|---|
| Filler | Greater than +/- 10% |
| Disintegrant<br>starch<br>other | <br>Greater than +/- 6%<br>Greater than +/- 2% |
| Binder | Greater than +/- 1% |
| Lubricant<br>calcium or magnesium stearate<br>other | <br>Greater than +/- 0.5%<br>Greater than +/- 2% |
| Glidant<br>talc<br>other | <br>Greater than +/- 2%<br>Greater than +/- 0.2% |
| Film coat | Greater than +/- 2% |

Figure 3

Table 7. Level 1 Component and Composition Changes for Modified Release Oral Solid Dosage Forms (release controlling excipient)

| Excipient | Percent Excipient (w/w) Out of Total Release Controlling Excipient Content in the Modified Release Solid Oral Dosage Form |
|---|---|
| Any release controlling excipient(s) | +/- 5% |

Table 8. Level 2 Component and Composition Changes for Modified Release Oral Solid Dosage Forms (release controlling excipient)

| Excipient | Percent Excipient (w/w) Out of Total Release Controlling Excipient Content in the Modified Release Solid Oral Dosage Form |
|---|---|
| Any release controlling excipient(s) | +/- 10% |

Table 9. Level 3 Component and Composition Changes for Modified Release Oral Solid Dosage Forms (release controlling excipient)

| Excipient | Percent Excipient (w/w) Out of Total Release Controlling Excipient Content in the Modified Release Solid Oral Dosage Form |
|---|---|
| Any release controlling excipient(s) | Greater than +/- 10% |

Figure 4

Table 10. Schematic of use within the commercial pipeline

Table 11. Composition of Aspirin Formulations

| Component | Formulation A1 (mg/tab) | Formulation A2 (mg/tab) | Formulation A3 (mg/tab) |
|---|---|---|---|
| Aspirin | 325 | 325 | 325 |
| Microcrystalline cellulose | 73 | 83 | 63 |
| Magnesium stearate | 2 | 2 | 2 |
| TOTAL WEIGHT | 400 | 410 | 390 |

Table 12. Composition of Prednisone Formulations

| Component | Formulation B1 (mg/tab) | Formulation B2 (mg/tab) | Formulation B3 (mg/tab) |
|---|---|---|---|
| Prednisone | 5 | 5 | 5 |
| Microcrystalline cellulose | 94.5 | 94.5 | 94.5 |
| Magnesium stearate | 0.5 | 0.75 | 0.25 |
| TOTAL WEIGHT | 100 | 100.25 | 99.75 |

Table 13. Composition of Indomethacin Formulations

| Component | Formulation C1 (mg/tab) | Formulation C2 (mg/tab) | Formulation C3 (mg/tab) |
|---|---|---|---|
| Indomethacin | 25 | 25 | 25 |
| Microcrystalline cellulose | 71.5 | 74 | 69 |
| Croscarmellose sodium | 3 | 2 | 4 |
| Magnesium stearate | 0.5 | 0.5 | 0.5 |
| TOTAL WEIGHT | 100 | 101.5 | 98.5 |

Table 14. Compositions of Acyclovir Formulations

| Component | Formulation D1 (mg/tab) | Formulation D2 (mg/tab) | Formulation D3 (mg/tab) |
|---|---|---|---|
| Acyclovir | 200 | 200 | 200 |
| Microcrystalline cellulose | 113.26 | 120.26 | 106.26 |
| Starch | 35 | 27.99 | 41.99 |
| Magnesium stearate | 1.75 | 1.75 | 1.75 |
| TOTAL WEIGHT | 350 | 350 | 350 |

Figure 6

Table 15. 2nd Derivative of Absorbance vs. Wavelength: Aspirin Formulations

Table 16. 2nd Derivative of Absorbance vs. Wavelength: Prednisone Formulations

Table 17. 2nd Derivative of Absorbance vs. Wavelength: Indomethacin Formulations Table 18. 2<sup>nd</sup> Derivative of Absorbance vs. Wavelength: Acyclovir Formulations

DRUG AUTHENTICATION

BACKGROUND

1. Field of the Invention

This invention relates generally to a method for assuring drug and drug product identity as a product is distributed from the manufacturer to the retailer and to the patient. This invention allows for the active evasion of the counterfeiting of pharmaceutical products.

Within the distribution system of drugs and drug products, there is a need to assure drug and drug product identity. Example scenarios include the need to identify and differentiate authentic and counterfeit drug products, and a need to assure the dispensing of the correct drug product to patients from pharmacies. There also exists the need to authenticate the manufacturer of drugs after they leave the pharmacy, such as when a drug is allegedly involved in causing injury to a patient.

Drug product counterfeiting is a significant and growing world-wide problem. There are about 9 billion subscriptions filled worldwide each year; about 3 billion prescriptions are filled in USA. It has been estimated that about 10 to 50 percent of prescription drugs in certain countries of Asia, Africa, and South America may be counterfeit. The number of counterfeit drug cases being investigated by the FDA has quadrupled and includes such well known drugs as Lipitor, Procrit, Neupogen, Serostim, Zyprexa, Viagra, and Evra. Drugs are now purchased in increasing quantities over the Internet and from Canadian and Mexican pharmacies making source and drug identification even harder.

In "Combating Counterfeit Drugs: A Report of the Food and Drug Administration", a number of different technologies to prevent counterfeiting are discussed, such as multi-pronged approaches utilizing tag technologies (e.g. track-and-trace) pedigree papers, an electronic package code (EPC), bar codes, radio frequency ID (FRID), special inks, holograms, strengthening state licensure requirements for wholesale distributors, and continuing development and implementation of secure business practices. Also discussed is requiring manufacturers to sell products only to wholesalers who only directly purchase from the manufacturer and requiring manufacturers to publish the names of their wholesalers on their Web sites In addition to problems of counterfeiting, with the increasing number of prescriptions being filled, there is an increased chance for prescription error. While these errors may take many forms, the likelihood of a dangerous or life threatening "adverse drug event" increases proportionally with the increased chance of prescription fill error. Several studies have shown that prescription error rates are consistently in the 2% to 7% range, with a 4% error rate often cited as a reliable average.

Many systems have been devised to apply identifying markers to drugs, such as color, size and shape distinctions among different drugs or on the same drug from different manufacturers. Identification markers applied to drugs are typically discernible to a prospective counterfeiter and can therefore be reproduced by the counterfeiter in many cases.

One of the problems confronting marking systems relating to drugs is the need to provide unadulterated drugs, i.e. drugs which the FDA considers to be subject to federal guidelines and which meet those guidelines. Thus, the addition of marker substances to a dosage form, although not discernable without sophisticated analysis procedures, must meet regulatory approval and is typically subject to onerous reporting requirements. Furthermore, counterfeiters can also analyze the drug for the presence of the marker and thereafter duplicate the marker containing drug.

Thus, there exists an unfulfilled need for a drug identification system which is covert, which is within governmental guidelines for pharmaceutical quality, which can quickly determine the source and/or identity of the drug as to manufacturer, including the production lot, and which, optionally, may be maintained in confidence from the identification system user. Ideally, the identification system is a dynamic system that changes over time, thereby rendering efforts to break the system even more unlikely to be successful.

2. Description of Related Art

Color, shape size and external markings have long been used to identify drugs in solid dosage forms to be used in conjunction with external container labeling schemes.

There are examples of overt drug labeling systems known to the art. Baum, U.S. Pat. No. 4,918,604, describes a drug labeling and prescription filing system. The system identifies the dispensed drug to be identified via a color photograph of the drug on its packaging.

An example using a combination of overt methods is disclosed in Wootton, U.S. Pat. No. 6,535,637 and entitled Pharmaceutical Pill Recognition and Verification System. The system utilizes a combination of coloration, shape, size and other surface features of the pill or tablet.

A scheme using covert identification of a drug by spectral means is disclosed in Soloman, U.S. Pat. No. 5,679,954 entitled Non-Destructive Identification of Tablet Dissolution by Means of Infared Spectroscopy and U.S. Pat. No. 5,900,634 entitled Real-Time On-Line Analysis of Organic and Non-Organic Compounds for Food, Fertilizers, and Pharmaceutical Products. Soloman provides an apparatus for infrared spectroscopy using a succession of collimated light beams throughout the middle and near infrared spectrum. These beams are impinged against the sample and the diffuse component of the reflected light is measured throughout the spectrum. Finally, the light received is analyzed by a neutral network to determine the sample characteristics.

Rzasa et al., U.S. Pat. No. 6,771,369. entitled System and Method for Pharmacy Validation and Inspection, discloses an apparatus for verifying the identity of a dispensed pharmaceutical. An analysis unit adapted to determine a property of the dispensed pharmaceutical, an input device adapted to receive predetermined identifying information corresponding to the dispensed pharmaceutical, and a comparison unit adapted to compare the determined property of the dispensed pharmaceutical with the predetermined identifying information. Rzasa et al. also discloses a method of verifying a prescription, wherein the prescription comprises a pharmaceutical compound, by associating the prescription with a unique identifier, storing the unique identifier, determining the identity of the pharmaceutical compound, and comparing the identity of the pharmaceutical compound with the unique identifier.

BRIEF SUMMARY OF THE INVENTION

This present disclosure uses spectral analyses, such as near-infrared (NIR) spectroscopy, to verify and identify pharmaceutical products through their product signatures. A method is disclosed where an amount of one or more of the inactive ingredients in the pharmaceutical product is varied over time; the variation providing a different product signature, but falling within a level deemed permissible by a regulatory body. This method results in the convert inclusion of unique product signatures that can be changed over time between batches of product, resulting in an authentication system that is difficult to deceive by potential counterfeiters.

The marking system is covert since the authentication system employs a pharmaceutical product's NIR spectrum. The marking system is inherent in the drug itself, is present in each solid dosage form of the drug, and cannot be modified after manufacture. Inert ingredients in the dosage form are changed over time, the spectral signature of the dosage form is determined by the producer [reference] or third party vendor setup for such purposes and an unknown sample has its spectral signature compared to the spectral signature of the reference. The match or lack of match of the two spectral signatures determines whether or not the dosage form was produced by that manufacturer, and, if produced by that manufacturer, which batch, lot, plant, manufacturing line, or time of manufacture, etc. the set of dosage forms the sample belongs to.

The present method allows a manufacturer to "fingerprint" or "authenticate" a selected quantity of manufactured drug, be it by batch, by production location, by production line, by date of manufacture, etc. The word "authenticate" as used herein refers to analysis based on a parameter or set of parameters associated with a pharmaceutical product that allows an observer to determine some fact relating to the product and thereafter to compare that fact to a reference standard. Information developed may be used to identify the drug, such as a therapeutic agent, a non-therapeutic agent (excipient), an origin, dosage level, and the like.

Due to its flexibility in determining the number of dosage forms manufactured with a single product signature, the manufacturer can use the methods of the present invention for quality assurance, quality control, or other internal or external control purposes. The product signature is used in conjunction with packaging information to confirm lots, batches or any other identifying information as the pharmaceutical product moves through the supply chain.

These benefits are obtained by verifying and/or determining identity of pharmaceutical products within a drug product distribution system, and are achieved though the use of NIR techniques optionally in connection with one or more other technologies. The combination of these techniques and approaches make for a rapid and accurate approach to assure drug and drug product identity, as well as a method to prevent the pharmaceutical product from being counterfeited.

The methods also provide an efficient technique for fingerprinting drugs as to the manufacturer and production batch. Most significantly, the techniques disclosed provide for systems and methods of manufacturing a unique fingerprint that serves as a label or product signature inherent in each pharmaceutical product or batch thereof. Advantageously, the reference product signature is selectively disclosed and easily coordinated through the manufacturer of the pharmaceutical product.

The herein disclosed approach is to apply NIR spectroscopy with a manufacturing method that provides for a dynamic tag system. Future tags are not anticipatable and perhaps not practically detectable since formulation component(s) themselves provide the tag.

In certain embodiments, the manufacturing method complies with regulatory mechanisms that were implemented in 1995 (immediate release products) and 1997 (modified release products) to minimize regulatory review or reporting requirements. The method may be modified as regulatory or equipment changes occur to maintain or increase the number of signatures that may be used.

NIR spectrometry is advantageous in terms of time and disposables. NIR is noninvasive and nondestructive. Analysis times are very short (e.g. 1 sec) and additional reagents are not required. The procedure is highly sensitive and is able to can perform multi-component analyses, as disclosed herein. Moreover, the disclosed procedures require little, if any, sample preparation.

In one of its various embodiments, the present invention is a method of labeling a pharmaceutical product having one or more active ingredients and one or more inactive ingredients comprising varying an amount of at least one of the one or more inactive ingredients over time and generating a product signature of the pharmaceutical product having the varied amount of the at least one of the one or more inactive ingredients.

The present invention includes a batch identification method for determining the source of a pharmaceutical product from among a plurality of production batches of the pharmaceutical product, where the pharmaceutical product has one or more active ingredients and one or more inactive ingredients, comprising changing an amount of at least one of the one or more inactive ingredients among different batches of the pharmaceutical product produced, the variation being at least sufficient to distinguish the difference in the NIR spectra of product produced in each batch.

Also disclosed is a system for verifying the authenticity of a pharmaceutical product comprising the steps of: manufacturing more than one batch of a pharmaceutical product, each batch having a reference spectral signature; inputting each of the reference spectral signatures into a database; scanning a sample pharmaceutical product to produce a scanned spectral signature; comparing the scanned spectral signature to each of the reference spectral signatures; and reporting the results of the comparison, wherein the authenticity of the sample pharmaceutical product is verified by the scanned spectral signature being equivalent to at least one of the reference spectral signatures.

In another of its embodiments the invention comprises a set of groups of a pharmaceutical product having one or more active ingredients and one or more inactive ingredients, wherein the one or more active ingredients and the one or more inactive ingredients are the same in each group in the set, and an amount of at least one of the one or more inactive ingredients is different in at least one group of the set as compared to the other groups in the set, wherein the amount is detectable in a near-infrared (NIR) spectra of the pharmaceutical product in the at least one group of the set as compared to a near-infrared (NR) spectra of the pharmaceutical product of the other groups of the set.

As used in this disclosure, a "set" of groups of pharmaceutical products means a plurality of groups where each group is related to the other groups in the set by having the same active and inactive ingredients present in the pharmaceutical product, each group being distinguished from other groups in the set by having varying amounts of one or more of the inactive ingredients in the pharmaceutical product.

The invention also includes member[s] of a set of groups of a pharmaceutical product having one or more active ingredients and one or more inactive ingredients, wherein the one or more active ingredients and the one or more inactive ingredients are the same in each group in the set, and an amount of at least one of the one or more inactive ingredients is different in at least one group of the set as compared to the other groups in the set, wherein the amount is detectable in a near-infrared (NIR) spectra of the pharmaceutical product in the at least one group of the set as compared to a near-infrared (NIR) spectra of the pharmaceutical product of the other groups of the set.

In yet another embodiment, the present invention is a method of manufacturing a labeled pharmaceutical product having one or more active ingredients and one or more inactive ingredients comprising modifying the quantity of at least one of the one or more inactive ingredients in a first pharmaceutical product to make a second pharmaceutical product, wherein the modification is detectable in an near-infrared (NIR) spectra of the second pharmaceutical product as compared t a near-infrared (NIR) spectra of the first pharmaceutical product, wherein said second pharmaceutical product is the labeled pharmaceutical product.

The present invention further includes a labeling system for a pharmaceutical product having one or more active ingredients and one or more inactive ingredients comprising modifying a quantity of at least one of the one or more inactive ingredients in a first pharmaceutical product to make a second pharmaceutical product, wherein the modification is detectable in a near-infrared (NIR) spectra of the second pharmaceutical product as compared to a NIR spectra of the first pharmaceutical product, wherein said second pharmaceutical product comprises the label.

In yet another of its various embodiments, the present invention discloses a method of determining the identify of a pharmaceutical product comprising the steps of obtaining a product signature of said pharmaceutical product and comparing said product signature to a reference product signature of a reference pharmaceutical product, wherein said reference product signature is a member of a library, wherein the pharmaceutical product is identified as the reference pharmaceutical product if the product signature of the pharmaceutical product is the same as the reference product signature.

BRIEF DESCRIPTION OF THE FIGURES

FIG. 1 contains Table 1. Level 1 Component and Composition Changes for Immediate Release Oral Solid Dosage Forms and Table 2. Level 2 Component and Composition Changes for Immediate Release Oral Solid Dosage Forms FIG. 2 contains Table 3. Level 3 Component and Composition Changes for Immediate Release Oral Solid Dosage Forms and Table 4. Level 1 Component and Composition Changes for Modified Release Oral Solid Dosage Forms (nonrelease controlling excipient)

FIG. 3 contains Table 5. Level 2 Component and Composition Changes for Modified Release Oral Solid Dosage Forms (nonrelease controlling excipient) and Table 6. Level 3 Component and Composition Changes for Modified Release Oral Solid Dosage Forms (nonrelease controlling excipient)

FIG. 4 contains Table 7. Level 1 Component and Composition Changes for Modified Release Oral Solid Dosage Forms (release controlling excipient); Table 8. Level 2 Component and Composition Changes for Modified Release Oral Solid Dosage Forms (release controlling excipient); and Table 9. Level 3 Component and Composition Changes for Modified Release Oral Solid Dosage Forms (release controlling excipient)

DETAILED DESCRIPTION OF THE INVENTION

Figure 5:
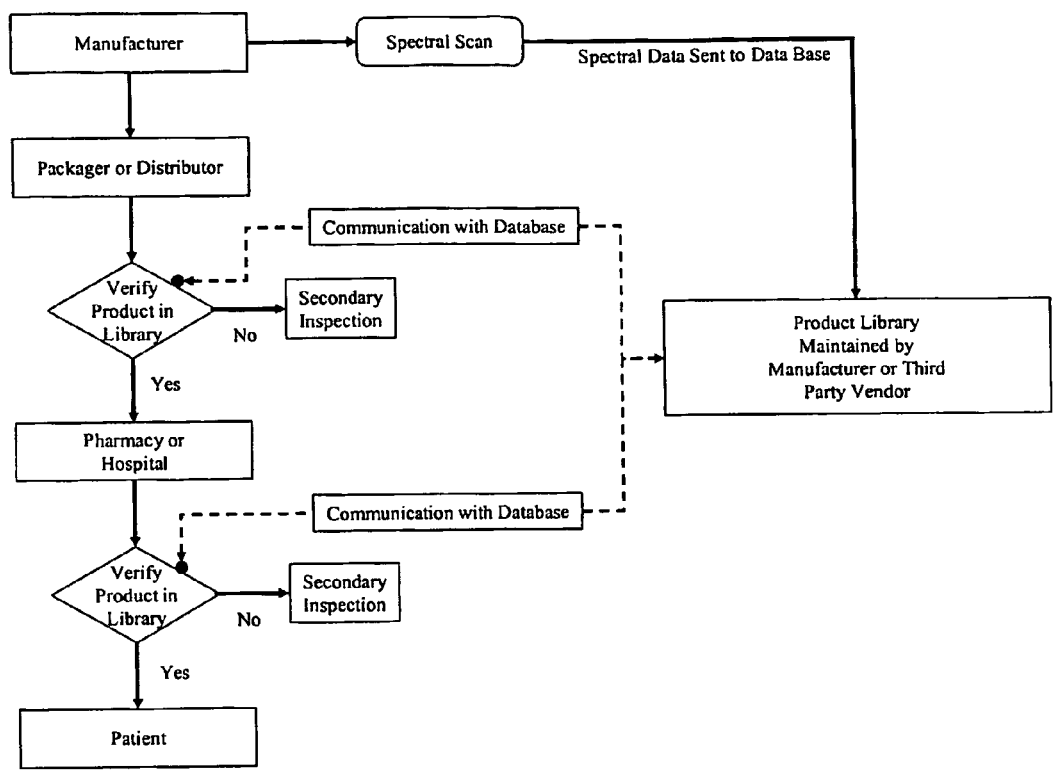
FIG. 5 contains Table 10. Schematic of areas of use within the commercial pipeline FIG. 6 contains Table 11. Composition of Aspirin Formulations; Table 12. Composition of Prednisone Formulations; Table 13. Composition of Indomethacin Formulations; and Table 14. Compositions of Acyclovir Formulations.
Figure 7:
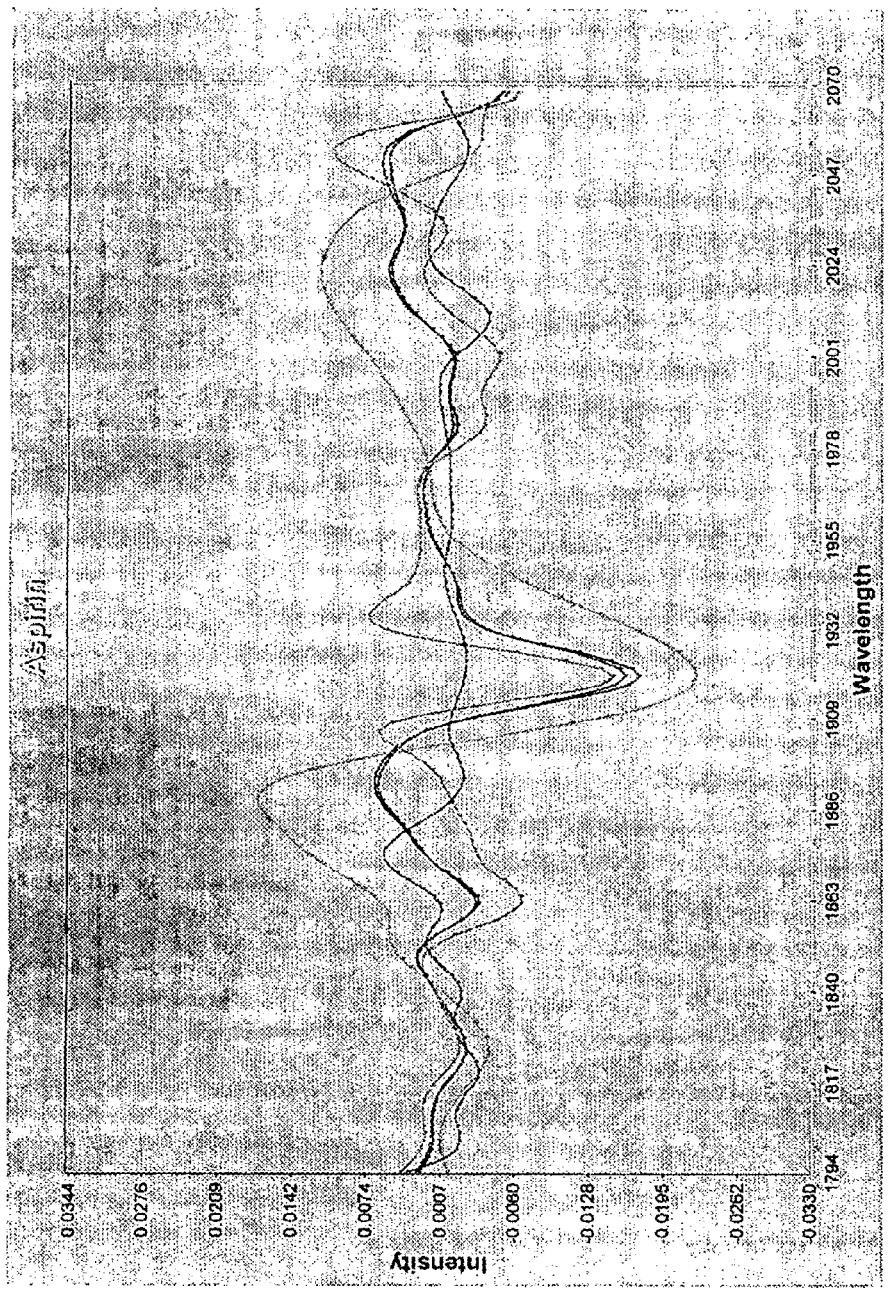
FIG. 7 contains Table 15. This is a chart of the $2^{nd}$ Derivative of Absorbance Versus Wavelength: Aspirin Formulations where formulations A3 (Yellow), A1 (Blue), and A2 (Red) contained increasing amounts of microcrystalline cellulose, the intensities around 1995 nm and 2055 nm reflect NIR to differentiate the formulations and the profiles of pure microcrystalline cellulose (Light Blue) and pure aspirin (Green) are also shown.
Figure 8:
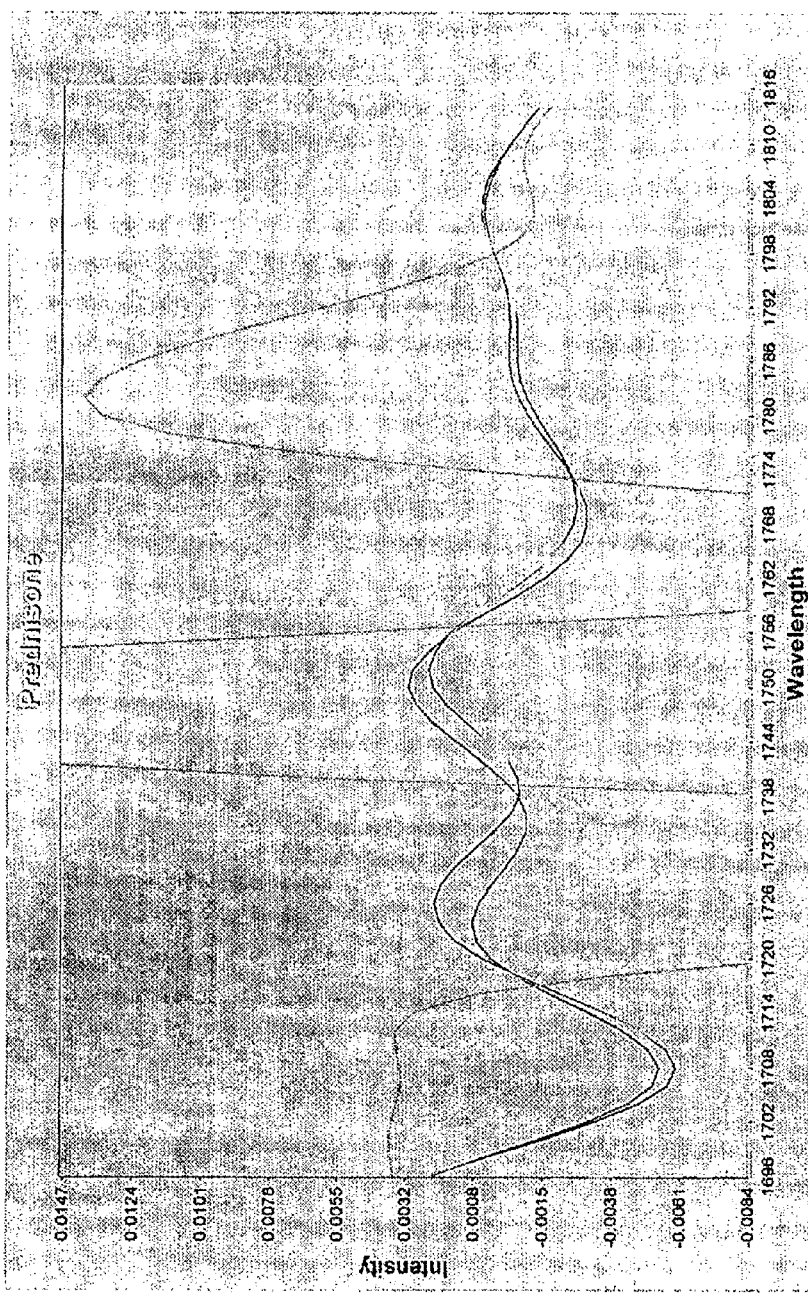
FIG. 8 contains Table 16. This is a chart of the $2^{nd}$ Derivative of Absorbance Versus Wavelength: Prednisone Formulations where formulations B3 (Yellow), B1 (Blue), and B2 (Red) contained increasing amounts of magnesium stearate, the intensities around 1705 nm, as well as the regions between 1725-1735 nm and 1775-1790 nm, reflect NIR to differentiate the formulations and the profile of pure magnesium stearate (Light Blue) is also shown.
Figure 9:
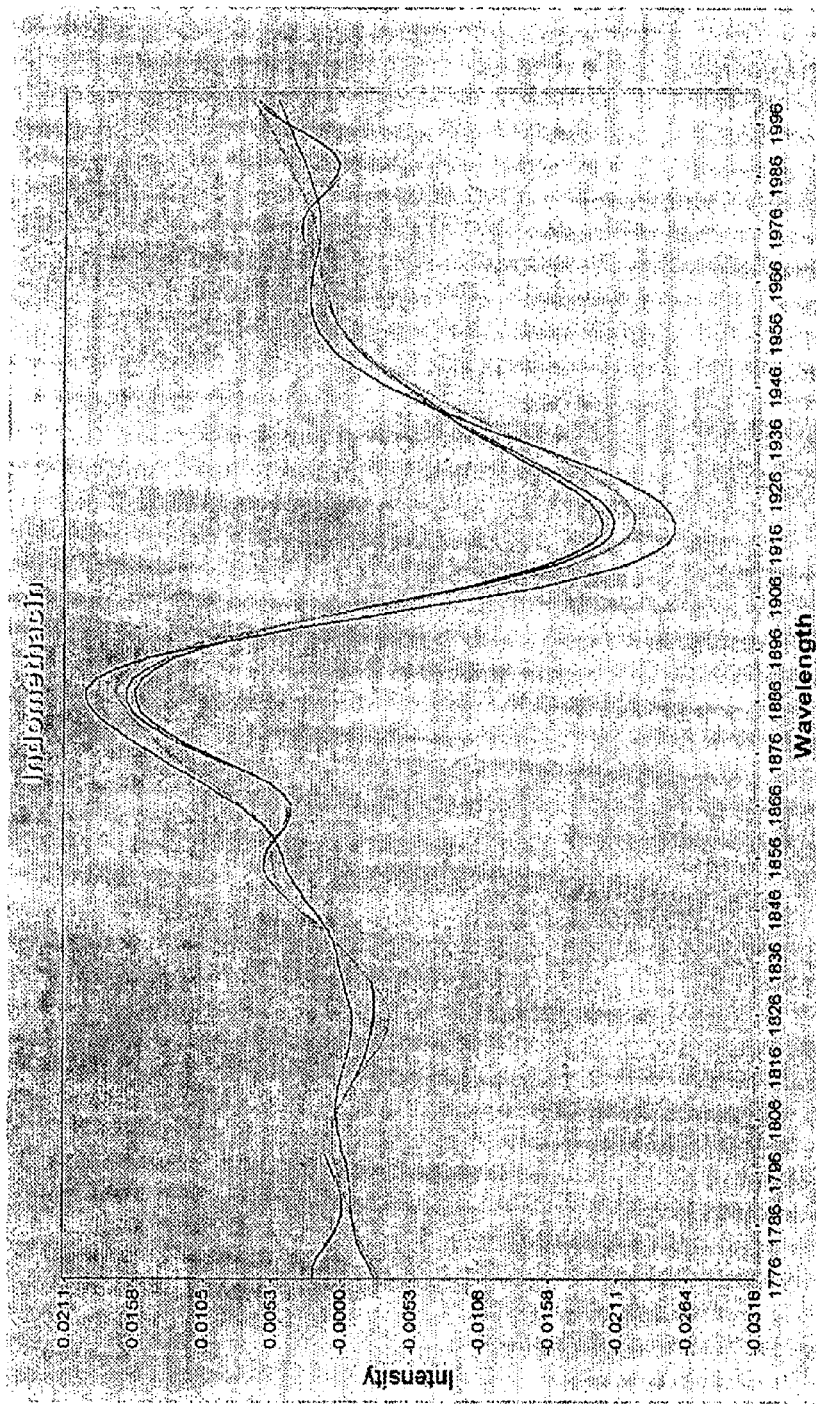
FIG. 9 contains Table 17. This is a chart of the $2^{nd}$ Derivative of Absorbance Versus Wavelength: Indomethacin Formulations where formulations C3 (Yellow), C1 (Blue), and C2 (Red) contained increasing amounts of microcrystalline cellulose, as well as decreasing amounts of croscarmellose sodium, the intensities around 1890 nm and 1920 nm reflect NIR to differentiate the formulations and the profiles of pure microcrystalline cellulose (Light Blue) and pure croscarmellose sodium (Purple) are also shown.
Figure 10:
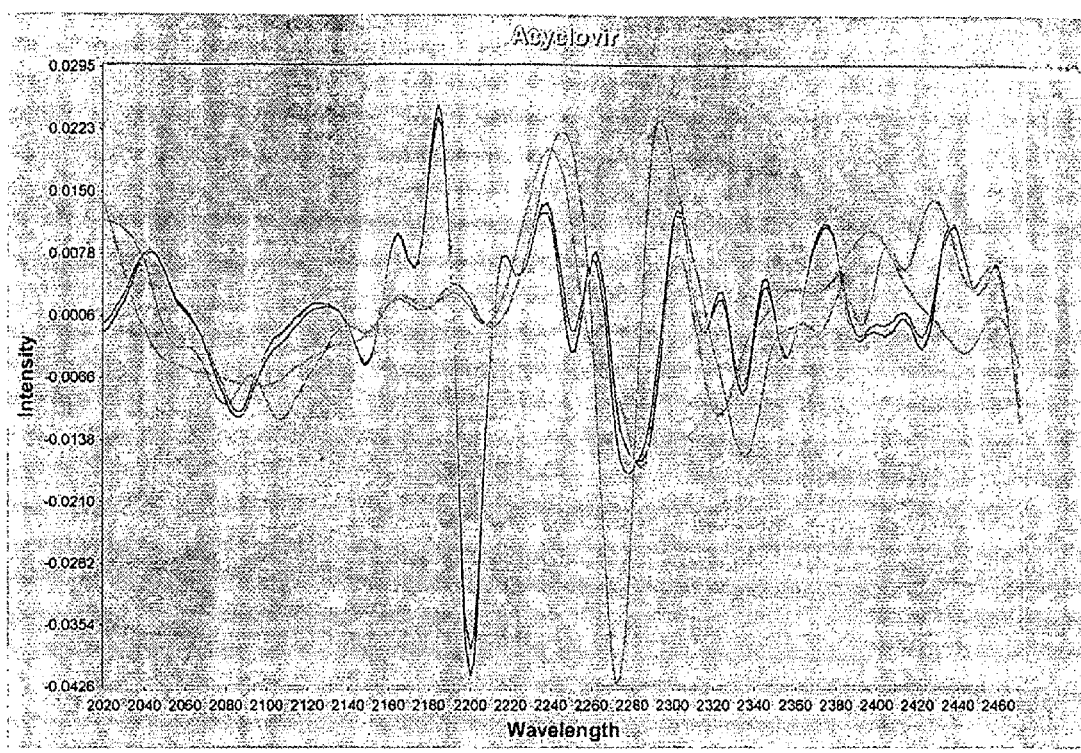
FIG. 10 contains Table 18. This is a chart of the $2^{nd}$ Derivative of Absorbance Versus Wavelength: Acyclovir Formulations where formulations C3 (Yellow), C1 (Blue), and C2 (Red) contained increasing amounts of microcrystalline cellulose, as well as decreasing amounts of starch where the intensities around 2175 nm, 2205 nm, 2225 nm, 2250 nm, 2265 nm, 2320 nm, 2345 nm, 2365 nm, as well as the regions between 2100-2130 nm and 2380-2420 nm, reflect NIR to differentiate the formulations, and the profiles of pure microcrystalline cellulose (Gray) and pure starch (Light Blue) are also shown.

When used in this specification, the following words and phrases have the following meanings ascribed to them.

A "pharmaceutical product" is a dosage form that comprises one or more therapeutic agents and one or more inactive ingredients.

"Therapeutic agents" include natural [biologics] drugs, synthetic drugs and nutraceuticals.

"Dosage forms" include, by way of example, tablets, capsules, powders, solutions, semisolids, suppositories, and lyophilized and milled powders, which may be reconstituted for injection.

"Drugs" include by way of example, atorvastatin calcium, azithromycin, amlodipine besylate, carbamazepine, ceftriaxone sodium, clozapine, epoetin alfa, filgrastim, indinavir sulfate, isotretinoin, lamivudine/zidovudine, leuprolide acetate, olanzapine, phenyloin sodium, somatropin, trovafloxacin mesylate, and warfarin sodium.

"Nutraceuticals" include by way of example, feverfew, *ginkgo biloba*, saw palmetto, St. John's Wort, chondroitin sulfate, Coenzyme Q10, glucosamine, growth hormones, L-carnitine, L-phenylalanine, shark cartilage, vegetable concentrates, chromium picolinate, manganese, biotin, riboflavin, and ascorbic acid.

The identity of a pharmaceutical product minimally denotes the therapeutic agent (or therapeutic agents) contained in the pharmaceutical product, the dose or concentration of each therapeutic agent in the pharmaceutical product, and manufacturer of the pharmaceutical product or any combination thereof.

"Counterfeit" denotes a product that has been mislabeled or otherwise adulterated with respect to identity and/or source. A product manufactured by an unapproved source is counterfeit.

A "counterfeit pharmaceutical product" is dosage form that is counterfeit and which may or may not comprise a therapeutic agent.

Authentic denotes not being counterfeit. An authentic pharmaceutical product is a pharmaceutical product that is not counterfeit.

A "dispensing error" is the dispensing of a pharmaceutical product which is not the pharmaceutical product specified in the dispensed prescription label.

A "product signature" is the spectral features obtained from a pharmaceutical product or counterfeit pharmaceutical product that is subjected to one or more spectral analyses. Methods of spectral analysis include near-infrared (NIR) spectroscopy, Raman spectroscopy, and laser induced fluorescence (LIF) spectroscopy. An example of a product signature is the near-infrared spectrum of a specific lot of predinisone tablets that were produced by a specific manufacturer. Near-infrared spectrum is the absorption spectrum between 400 and 2500 nm.

A "library" of product signatures is a collection of product signatures.

An "inactive ingredient" is a component of a pharmaceutical product which has no intended therapeutic effect; inactive ingredients are also known as excipients.

In the method disclosed, covert NIR spectral fingerprints are embedded into each lot of a pharmaceutical formulation by modifying formulation ingredient quantities while remaining within regulatory agency allowed composition changes. Among the significant benefits of this approach are no need for an external taggant and minimal regulatory burden. By intentionally varying excipient quantities within allowed ranges, it is possible to encode a unique fingerprint into each product lot.

Counterfeit drug products are an increasing problem, particularly because counterfeiting technology and counterfeiters have become more savvy. There remains a need to detect counterfeit drugs, including counterfeit drugs that are prepared and/or packaged similarly to the authentic pharmaceutical products. The invention includes but is not limited to the use of near-infrared (NIR), Raman and LIF (laser induced fluorescence) spectroscopy (all possible methods will hence be referred to as spectral methods or NIR methods) to identify the source of a drug in particulate dosage form and/or packaging. Advantages of NIR spectroscopy include its non-invasiveness, potential for low detection limits, rapidity of analysis (approximately 1 second), and minimal or no sample preparation. The vast majority of components commonly found in a pharmaceutical product exhibit a NIR spectrum.

Either or both the pharmaceutical packaging or dosage form can serve as taggants. For example, embossing, imprinting, printing, coating, dosage form size, and other identification methods can be applied to change the physical appearance of the dosage form (e.g. subtle changes in logo, use of an ultraviolet-dependent dye). Such approach can be used alone or in combination with other modifications of packaging and/or changes in the dosage form.

In a particular embodiment, the components in the dosage form can be varied, approximately batch-to-batch or with other [arbitrary] frequency, to provide a distinctive spectral signature for the product from that batch or lot.

Components of an oral particulate dosage forms (e.g. tablets or capsules) include the drug (active ingredient), impurities, drug degradents, fillers, disintegrants, binders, lubricants, glidants, colorants, flavoring agents, and coating materials. Some or all of the component levels can be modified, either batch-to-batch or with some other frequency, to yield a NIR spectra for the batch, a set of batches or other identification of lots.

Utilizing the procedures disclosed herein, the NIR spectra would not be identical for all product lots. A certain batch of product, or certain set of product batches, will have a unique composition, and hence a unique NIR spectra. The NIR spectrum of a particular lot is disclosed solely to those persons or entities selected by the manufacturer. Only the manufacturer (or agents of the manufacturer) will know the composition and associated NIR spectra of products from a particular batch or lot.

A suspect product can be subjected to NIR analysis and cross-referenced against the authentic NIR spectra. The association between authentic product's batch number and its NIR spectra, along with the ease of measuring NIR spectra, provides a basis to combat counterfeit drugs, to allow quality control and to identity lots for sundry other purposes.

Of added benefit, the association between NIR spectra and batch number(s) need not be provided to regulatory agencies or enforcement officials or health care providers, who could still perform field sampling and relay NIR spectra to the manufacturer. The manufacturer would then report back only the information of whether or not the sample matches the lot associated with that speactrum.

Furthermore, because the manufacturer would arbitrarily vary the variation of ingredients within the drug, past compositions (i.e. past NIR spectra of previous batches) would not be indicative of future compositions (i.e. future NIR spectra). Hence, a counterfeit effort would have no target product to counterfeit, without detection.

This approach employs the visible and NIR region of the electromagnetic spectrum. The NIR region typically includes wavelengths between about 700 nm (near the red in the visible spectrum) and about 3000 nm (near the infrared stretches of organic compounds). NIR absorbance peaks originate from overtones and combinations of the fundamental (mid-IR) bands and from electronic transitions in the atoms. C—H, N—H, and O—H bonds are responsible for most of the major absorbances. NIR spectrometry is used chiefly to identify or quantify molecules, including unique hydrogen atoms. NIR spectrometry is used to analyze for water, alcohols, amines, and any compounds containing C—H, N—H, and/or O—H groups. Many other bond combinations also provide NIR absorbance peaks. The visible region includes wavelengths between about 400 nm to about 700 nm. Absorbance peaks in this region can originate from conjugated pi electrons or aromatic moieties. Lakes and dies commonly used to give a dosage from a unique color typically absorb in this region of the electromagnetic spectrum While a pharmaceutical product typically has only one formula, and while manufacturers typically avoid manufacturing changes, this new approach to combat counterfeiting relies on the availability of several (i.e. more than one) formulas for the marketed product.

The U.S. Food and Drug Administration (FDA) allows for a range of component and composition changes in the manufacturing of products, without onerous regulatory requirements. The Center for Drug Evaluation and Research [CDER] publishes a series of monographs in its "Guidance for Industry" series. Its monographs "Scale-Up and Postapproval Changes: Chemistry, Manufacturing, and Controls: In Vitro Dissolution Testing and In Vivo Bioequivalence Documentation" [SUPAC monographs] deal with changes in various dosage forms and allowable changes in those dosage forms and reporting requirements relating to those changes. Monograph CMC 5 entitled "Immediate Release Solid Oral Dosage Forms" provides for certain changes in excipients in immediate release dosage forms in section "III. Components and Composition". CMC 8 is the analogous document relating to modified release dosage forms.

Section III of these monographs relates to changes in excipients [but not active components] in drug products and categorizes changes in excipient levels into three groups. In the case of immediate release and modified release oral solid dosage forms, changes are denoted Level 1, Level 2, and Level 3 type changes. Level 1 changes are those that are unlikely to have any detectable impact on formulation quality and performance; regulatory filing documentation of a Level 1 change is limited to the Annual Report. Level 2 changes are those that could have a significant impact of formulation quality and performance. Level 3 changes are those that are likely to have a significant impact of formulation quality and performance. Tests and filing documentation for a Level 2 change and a Level 3 change each vary depending upon three factors: drug therapeutic range, drug solubility, and drug permeability. Tables 1-9 describe these manufacturing changes.

The present invention may be used within any countries public health infrastructure. In such cases, the skilled artisan is aware of obtaining and applying the appropriate regulatory guidelines in the manners referred to in the non-limiting exemplary embodiments provided herein.

For example, in the United States, a Level 1 change requires less burdensome regulatory documentation, and represents one preferable example, relative to Levels 2 or 3 to vary formulation. Level 1 documentation requires one batch on long-term stability reported in an annual report. No additional dissolution documentation or in vivo bioequivalence documentation is required.

Hence, Level 1 changes are a preferable approach to tag authentic product, in order to avoid counterfeiting and facilitate the detection of counterfeiting through NIR spectroscopy. This approach avoids the use of a taggant that is fixed, or is one which is included in the formulation for the sole purpose as a taggant. Our approach to use the formulation's components themselves facilitates the tagging effort, and does so in a more subtle fashion, such that this tagging effort is less detectable and hence less counterfeitable.

For example, for each immediate and modified release oral solid dosage forms, a filler can be modified by as much as 5% to provide a NIR spectra that tags the authentic product, and still qualify as a Level 1 change. Given the ability of NIR spectroscopy to resolve 1% and smaller differences in formulation, a unique tag can be fabricated by varying the filler level. Moreover, the number of unique NIR signatures can be generated in a multiplicative fashion by modulating two or more components (e.g. vary filler, disintegrant, and binder). Varying filler over 11 levels, disintegrant over 7 levels, and binder over 3 level can results in 231 unique NIR spectra, or more.

It should be noted that the number of distinct spectra that can be obtained and/or used is limited only be the sensitivity of the test equipment. As the ability of the apparatus to distinguish among varying spectral data sets becomes greater, the number of tags available will increase and the required degree of excipient change will diminish A further limit on the system relates to the quality of the manufacturing process. As process controls become even more precise and the desirability of having such controls becomes known, manufacturing practices will be held to tighter tolerances and a greater number of different spectral signatures will become available.

It is contemplated that the spectral signature of different product groups will be used for quality assurance purposes and will be able to identify product produced by different manufacturers, different manufacturing facilities of the same manufacturer, different production lines within a manufacturing facility, or product produced by different shifts on the same line in a manufacturing facility.

By varying the signature over time, environmental effects on the product in the field can be tracked and maintained in a database. Varying signatures over time also allows inherent determination of product dating and whether the product in question is a post-expiration product.

While NIR spectroscopy has some previous limited application in pharmaceutical analysis, it has not been applied to combat counterfeit drugs. Our approach employs the formulation itself to provide a dynamic tag system and NIR spectroscopy. It does not employ a fixed tag or a tag whose sole function is to serve as a tag, and thus subject to counterfeiting.

The approach of applying NIR spectroscopy to a manufacturing method that provides for a dynamic tag system is novel. Future tags are not anticipatable, and perhaps not practically detectable since formulation component(s) themselves provide the tag. The manufacturing method makes use of regulatory mechanisms that were implemented in 1995 (immediate release products) and 1997 (modified release products), in order for the tag system to be dynamic, yet viable from a regulatory point of view.

NIR spectrometry is advantageous in terms of time and disposables. Analysis times are very short (e.g. 1 sec). It is sensitive to multi-component variables, as planned in the described approach. There is essentially no sample preparation. NIR is noninvasive and nondestructive. No reagents are required. Detection limits can be very low.

Also, because this device can detect the drug type and its dose this could also be used to greatly minimize the possibility of the pharmacist dispensing the wrong drug and the wrong dose of a drug In one embodiment, a unique NIR signature is engineered into the packaging as well as the product, much like a certificate of authenticity on a CD or commercial software package. A company could have several hundred types and assign a lot number to each one.

It should also be noted that varying the formulation to evade and detect counterfeiting is one approach in the application of spectral methods. Another approach does not make use of the intentional periodic variation of the formulation as described above.

Various applications for this technology include, but are not be limited to methods to evade and detect counterfeit drug products (and counterfeit drug substances and counterfeit excipients); methods to assure drug product distribution integrity (and drug substance integrity and excipient integrity) at different levels for monitoring drug product distribution, such as by pharmaceutical manufacturers, pharmaceutical wholesalers, pharmaceutical distributers, and pharmacies (who would be interested in detecting counterfeit drug products and in assuring the correct product is being dispensed.), pharmaceutical repackagers, and FDA field monitoring, as well as regulators in other countries.

A typical example application is in the detection of counterfeit drug products by FDA field inspectors and/or health care workers (e.g. pharmacist, nurse) working with the manufacturer of the authentic product. FDA field inspectors and/or health care workers would obtain the NIR spectrum of suspect products and relay the spectrum data to the manufacturer of the authentic product. Agents of the manufacturer of the authentic product could also inspect samples in the field by obtaining NIR spectrum of suspect products.

Another typical example of its use would be by pharmacies employing NIR to avoid accidental overdose or misadventure in pharmacy dispensing by assuring that the dispensing robot dispenses the correct product or to assure the dispensed product is the correct product with semi-automated dispensing devices where the NIR is built into tablet/capsule counter.

In one of its embodiments, the comparison data needed to reference the sample against authentic product is supplied to the field [the pharmacy, hospital or other dispensing authority] to allow them to determine the authenticity of the drug in the field.

In an alternative embodiment a more secure system is utilized, where the drug manufacturer maintains a comprehensive database of all variations of the drug dosage form over time and allows access to that database to authorized users to allow a multiplicity of data to be retrieved about the particular product being tested.

In a yet more secure variation, the manufacturer's central database reports only a yes: no answer as to whether the product is counterfeit or outdated, allowing the manufacturer to track the movement of its product through the supply chain but still maintain control over the dissemination of the information.

It is also contemplated that a central repository of such data may be set up by industry or government to track and maintain the purity of medicaments used by its citizens.

The following example is presented in order to more fully illustrate the preferred embodiments of the invention. It should in no way be construed, however, as limiting the broad scope of the invention.

EXAMPLE 1

Materials. The following drug substances and excipients were used as received: aspirin (Sprectrum, Gardena; Calif.), prednisone (Sigma; St Louis, Mo.), indomethacin (Spectrum; Gardina, Calif.), acyclovir (Spectrum; Gardena, Calif.), microcrystalline cellulose (Emocel 90M, Mendell; Patterson, N.Y.), magnesium stearate (Spectrum, Gardina, Calif.), croscarmellose sodium (FMC Biopolymer; Princeton, N.J.), starch (Lycatab C, Roquette; Lestrem, France), and lactose monohydrate (Super-tab, The Lactose Company; Hawera, New Zealand), Formulation Methods. Three tablet formulations were designed and evaluated for each of four drugs, such that 12 formulations were made. The four drugs were aspirin, prednisolone, indomethacin, and acyclovir, and are denoted as drug A, B, C, and D, respectively. The drugs differ in their therapeutic uses, physicochemical properties, spectral properties, and dose ranges. For each drug, three tablet formulations were fabricated. Tables 1-4 describe the composition of the 12 formulations and refer to formulations A1, A2, A3, B1, etc. In each table, the first formulations is denoted the reference formulation (i.e. A1, B1, C1, and D1 are reference formulations). For each drug, the formulations were varied within the SUPAC level 1 tolerances by varying one or more excipients, relative to the reference formulation, resulting in the second and third formulations (i.e. formulations A2 and A3 were variants for formulation A1; formulations B2 and B3 were variants for formulation B1).

Variant formulations were attained through the following changes, relative to the reference. For aspirin, microcrystalline cellulose was increased and decreased. For prednisone, magnesium stearate was increased and decreased. For indomethacin, microcrystalline cellulose and croscarmellose sodium were simultaneously varied. For acyclovir, microcrystalline cellulose and lactose monohydrate were simultaneously varied. In some cases the tablet weight changed.

Near-IR Methods. The formulations were scanned and analyzed by Foss NIRSystems Rapid Content Analyzer™. The following test conditions were used. Samples were placed into sealed glass scintillation vials and scanned in reflectance mode; each sample was scanned 62 times and averaged into one spectrum; the wavelength range was 400 nm to 2500 mm with samples collected every 2 nm. The raw spectral data were converted into absorbance and $2^{nd}$ derivative values using Foss's Vision software package.

Since the active components or components in the drug dosage for are not varied in the disclosed system, it is apparent that the system is not constrained by the type of active ingredient or combination of actives. It is within the ability and choice of a skilled artisan to chose the inactive ingredient or ingredients to vary in developing the various spectral profiles of a drug product regardless of its active ingredients.

It should also be apparent that the system is independent of the quantity of active ingredient in the dosage form and that the system may actually be used to provide a signature to distinguish among varying dosage forms.

While the system is not dependent upon the identity of the active ingredient or ingredients, it is recognized that the system may be most useful in conjunction with certain drugs that are more likely to be subject to theft, abuse or counterfeiting.

The invention claimed is:

1. A method of labeling and identifying a pharmaceutical product for verifying authenticity of the pharmaceutical product compared to a reference product comprising the steps of:
(a) preparing a batch of the pharmaceutical product comprising at least one active ingredient and at least one or more inactive ingredient,
(b) intentionally varying an amount of at least one of the one or more inactive ingredient in the batch of the pharmaceutical product from the amount in the reference product and wherein the step of intentionally varying the amount of the at least one of one or more inactive ingredient is within ranges allowed by a regulatory authority,
(c) scanning the batch of the pharmaceutical product with a near-infrared (NIR) spectrometer and obtaining a multi-wavelength NIR region absorption spectrum thereby generating a unique NIR region spectrum for the batch of the pharmaceutical product, and wherein the unique NIR region spectrum is different from a reference NIR region spectrum of the reference product, and
(d) inputting the unique NIR region spectrum for the batch to a database as a spectral signature for the batch of pharmaceutical product, thereby labeling and identifying the batch of the pharmaceutical product with the unique identifiable spectral signature for verifying authenticity of the batch of the pharmaceutical product.

2. The method of claim 1, wherein a plurality of production batches is prepared and the unique NIR region spectrum for each batch is saved to a central database.

3. The method of claim 1, wherein the at least one or more inactive ingredients whose amount is varied is a filler.

4. The method of claim 3, wherein an amount of the filler is that is varied is in a range of about minus 5 percent to about plus 5 percent based on a total weight of the pharmaceutical product.

5. The method of claim 1, wherein the at least one of one or more inactive ingredients whose amount is varied is a binder.

6. The method of claim 5, wherein an amount of the binder that is varied is in the range of about minus 0.5 percent to about plus 0.5 percent based on a total weight of the pharmaceutical product.

7. The method of claim 1, wherein the at least one or more inactive ingredient whose amount is varied is a disintegrant.

8. The method of claim 7, wherein the an amount of the disintegrant that is varied is in the range of about minus 3 percent to about plus 3 percent based on a total weight of the pharmaceutical product.

9. The method of claim 1, wherein the inactive ingredient whose amount is varied is a lubricant.

10. The method of claim 1, wherein the inactive ingredient whose amount is varied is a glidant.

11. The method of claim 1, wherein the inactive ingredient whose amount is varied is a film coat.

12. The method of claim 1, wherein the NIR spectrum of step (c), ranges from about 700 nm to about 3000 nm.

13. The method of claim 1, wherein the regulatory authority is the United States Food and Drug Administration (FDA).

14. The method of claim 2, wherein the central database is available to multiple users and used for a source of comparison to determine the authenticity of a batch of a pharmaceutical product.

\* \* \* \* \*